United States Patent [19]

Notari et al.

[11] 4,096,172
[45] Jun. 20, 1978

[54] CATALYTIC PROCESS FOR THE PRODUCTION OF ACRYLONITRILE

[75] Inventors: Bruno Notari; Vittorio Fattore, both of San Donato Milanese, Italy

[73] Assignee: Snam Progetti, S.p.A., Milan, Italy

[21] Appl. No.: 676,130

[22] Filed: Apr. 12, 1976

Related U.S. Application Data

[63] Continuation of Ser. No. 169,801, Aug. 6, 1971, abandoned.

[30] Foreign Application Priority Data

Aug. 7, 1970 Italy .............................. 28404 A/70

[51] Int. Cl.² ........................................... C07C 120/14
[52] U.S. Cl. ................................................. 260/465.3
[58] Field of Search ...................................... 260/465.3

[56] References Cited

U.S. PATENT DOCUMENTS 3,784,560  1/1974  Yoshino et al. .................. 260/465.3

Primary Examiner—Joseph Paul Brust
Attorney, Agent, or Firm—Morgan, Finnegan, Pine, Foley & Lee

[57] ABSTRACT

A process for preparing acrylonitrile comprising feeding propylene, ammonia and oxygen at ratios between 1/0.7/1 and 1/1.4/3 and at temperatures between 350° C. and 550° C., at pressures between 1 atm. and 5 atm. over a catalyst consisting essentially of one having the general formula:

$$W_a M_b Me_c \text{viii } O_d$$

wherein W is tungsten; M is bismuth; Me viii is iron; and O is oxygen, and wherein the tungsten is present in gram atomic amounts greater than the gram atomic amounts of each individual remaining metal component or the sum of the remaining components and $a$ is 1; $b$ is 0.04 to 0.8; $c$ is 0.08 to 0.8; and $d$ is 2.5 to 9.5, said catalyst having been calcined at a temperature in the range of from 400° C. to 800° C. for from 1 to 60 hours.

5 Claims, No Drawings

CATALYTIC PROCESS FOR THE PRODUCTION OF ACRYLONITRILE

This is a continuation of application Ser. No. 169,801 filed Aug. 6, 1971 now abandoned.

The present invention relates to a catalytic composition useful for the production of unsaturated nitriles and to a process for the production of said nitriles which makes use of said composition. More particularly, the present invention relates to a combination of elements, which combination is capable of promoting the production of unsaturated nitriles starting from olefins, ammonia and oxygen or gases containing oxygen.

In the art, processes are known for the production of unsaturated nitriles starting from olefins, ammonia and oxygen, said processes being based on the use of particular catalysts. Said catalysts are substantially a combination of elements, in practice of metal oxides or more generally of oxygenated compounds of particular metals.

Until now, however, on an industrial basis, substantially only few catalytic compositions have been successfully used; among them can be mentioned those comprising, as main constituent elements, molybdenum and bismuth. Many other compositions have been described in the art but they have had no industrial use. This is probably due to disadvantages noticed during experimentation with said compositions on an industrial or semi-industrial scale.

We have now found that a catalytic composition particularly useful for promoting the production of unsaturated nitriles is the one corresponding to the following formula:

$$W_a M_b Me_c^{viii} O_d$$

- wherein W is tungsten
  M is at least one metal selected from the class of promoters of the ammoxidation reaction and/or Bi;
  $Me^{viii}$ is a metal of the eighth group of the periodic table, in particular Fe, Co or Mi;
  O is oxygen;
  a, b, c, d are the numbers of the above-mentioned elements present in the composition.

In order to define said numbers, it is to be noted that they may be chosen from a wide range; but at least three metal elements must always be present and among them the relative amount of tungsten has to be at least equal to or bigger than the amount of each of the remaining metal elements or also equal to or bigger than the sum of their amounts; said amounts being gram atomic amounts. Oxygen must be present in such amount that the elements constituting the catalyst are in the form of oxygenated compounds.

Unrestrictively, if a is 1, b has a value chosen in the range between 0.04 and 0.8 and c a value in the range between 0.08 and 0.8 while d is the corresponding necessary number of oxygen atoms; therefore d is in the range between 2.5 and 9.5.

Said new compositions surprisingly and unexpectedly show the possibility of producing unsaturated nitriles with high selectivities and conversions in comparison with compositions which are not constituted by the same elements or containing them in different combinations.

Preferred compositions according to the invention, are the ones wherein $Me^{viii}$ is iron and M is chosen so as to include Bi, possibly combined with other promoters.

As to the proportions with which at least those three elements must be present, they have to be, as aforesaid, such that tungsten is present in a larger amount and at least bismuth and iron in an amount respectively in the range of from 4 and 8 hundredth of the gram-atoms of the W present to values of the magnitude order of the gram-atoms of the present tungsten. Amounts of Bi lower than those of Fe are preferred. When the compositions have more than three elements, the amounts of the other possible promoters of the ammoxidation reaction are within such ranges that the ratio of one gram-atom of promoter for each gram-atom of iron or bismuth is not exceeded.

As promoters of the ammoxidation reaction in this application we mean the elements listed below:

Among them, besides bismuth, we can choose oxides of elements of the groups III A, IV A, V A, VI A, I-B, 2-B, 3-B, 4-B, 5-B, 6-B, 7-B of the periodic system and preferably boron, tin, lead, phosphorus, antimony, sulphur, tellurium, copper, silver, zinc, cadmium, lanthanum, cerium, titanium, vanadium, chromium, manganese, rhenium.

The preparation of the composition of the invention does not present any difficulty for those skilled in the art. Said preparations consist essentially in solubilizing a salt, anhydride or acid of tungsten, a salt of the eighth group metal, preferably a nitrate, carbonate, acetate, and a salt or oxide of the other elements which are part of the catalytic composition.

Then the prepared solutions are mixed, obtaining a single solution or pulp which can be dried either by atomization or other suitable method. The resulting single solution can be alternatively subjected to coprecipitation, subsequent filtration and drying of the precipitate. Then, if necessary, we effect the working of the catalyst by extrusion or tabletting so as to give it a form more appropriate for its use in the reaction and the calcination of the same at a temperature in the range of from 400° C to 800° C, preferably from 500° C to 650° C, in a muffle in air or in a controlled atmosphere, the calcination time being in the range of from 1 hour to 60 hours.

The compositions of the invention are therefore combinations at least ternary of elements as before defined. The compositions may be constituted by mixtures of oxides or by very oxygenated compounds. They (the combinations) have the characteristic, when chosen among the preferred ones, of containing high melting point compounds which, as known, make the catalyst more resistant to thermal transformations and insure therefore a longer catalyst duration of life, and are subjected to a minor or to no loss of the constituent materials during the industrial working; further they have such mechanical characteristics that their use is possible both in fixed bed and fluid bed processes. They at least insure, as hereinbefore mentioned, selectivities and conversions entirely comparable with the ones of the best catalyst used on an industrial scale. Their behaviour during working is free from difficulties; experimentally we found that the catalytic combinations of the invention are active and selective also at temperatures slightly higher than the ones used for compositions having Bi as a substantial catalyst constituent.

Furthermore, it is surprising that water is not a critical element. While it is known that, in the case of other catalytic systems, its importance has been pointed out and it has been supposed that it has not only the physical task of removing heat but also the task of giving the catalyst a higher selectivity. Obviously, on an industrial scale, it will be possible to make use of water also with the composition which is the subject of this invention in order to remove better the heat product. Another beneficial effect of the compositions of the invention is the substantial absence of acrolein in the reaction products; and this consideration simplifies the operations in the plant purification section.

The compositions of the invention, as defined, constitute the active catalytic part to which, as required, various additives may be added in a manner known in the art. The compositions of the invention are further usefully employed as such or supported on a carrier; in said case there is no problem for the carrier which may be chosen from the materials known for this purpose as for instance silica, alumina and the like.

We can utilize the compositions of the invention in variable amounts over a wide range with regard to the carrier. For purpose of exemplification, said amounts are in the range of from 5% to 90% of the sum of the weights of the carrier and of the catalyst. As to the process for the production of unsaturated nitriles which makes use of the catalytic compositions of the invention, it consists substantially in feeding the olefin, oxygen (or the gas containing it) and ammonia on the catalyst as defined above. The process may be carried out in a fixed or fluid bed as aforesaid. The molecular ratios among the olefin, oxygen as such or in a gas containing it, and ammonia are in the range of from 1/1/0.7 to 1/3/1.4 as molecular ratios.

The reaction temperatures employed may vary over a wide range and may be chosen in the range of from 350° C to 550° C; the preferred temperatures being higher than 440° C and lower than 530° C.

Pressures may range between 0.7 and 7 atmospheres, the preferred pressures ranging from atmospheric pressure to 5 atmospheres.

The apparent contact time is in the range of from 0.1 to 20 sec., preferably from 0.5 to 10 inches. For contact time we mean the seconds during which the volume of the gaseous mixture to be treated, fed in unit time, is in contact with the catalyst unit volume, the volume of the gaseous mixture being measured at room temperature and at atmospheric pressure.

The starting olefin is chosen in accordance with the nitrile we want to obtain; in this way propylene will be useful for obtaining acrylonitrile, isobutylene for methacrylonitrile and higher olefins for the corresponding nitriles.

In the present description, the terms selectively and conversion are respectively indicated by:

Propylene conversion:
$$\frac{\text{moles } C_3H_6 \text{ fed} - \text{moles } C_3H_6 \text{ unreacted}}{\text{moles } C_3H_6 \text{ fed}} \times 100$$

Selectivity for acrylonitrile:
$$\frac{\text{moles of produced acrylonitrile}}{\text{moles } C_3H_6 \text{ fed} - \text{moles } C_3H_6 \text{ unreacted}} \times 100$$

Selectivity for acetonitrile:
$$\frac{\text{moles of produced acetonitrile}}{\text{moles } C_3H_6 \text{ fed} - \text{moles } C_3H_6 \text{ unreacted}} \times 100$$

For a better illustration of the invention we now report the following examples which in any case are to be considered unrestrictive of the same.

EXAMPLE 1

31 g of ammonium tungstate, 5 $(NH_4)_2O \cdot 12 WO_3 \cdot 4H_2O$ were weighed and poured in small portions into a glass wherein there was 50 cc of $H_2O_2$ at 35% b.w. We heated with stirring. The additions of ammonium tungstate were effected when the dissolution of the fractions previously added was completed. Separately in a beaker containing 100 cc of $H_2O$, 40 g iron nitrate, $Fe(NO_3)_3 \cdot 9H_2O$ were dissolved. Into the first solution, after cooling, the second was poured. 90 g silica "Ludox" at 40% were weighed and mixed with the solution of the tungsten and iron salts. The resulting solution was heated on an electrical heater, by stirring frequently up to dryness. The mass was calcinated in a muffle at 550° C during 4 hours. The catalyst at the end was milled, sieved and a fraction having a granulometry between 65 and 120 ASTM mesh was recovered.

Into a cylindrical stainless steel micro-reactor, 6 cc of catalyst were fed. The micro-reactor was heated in a small electrical oven. A thermo-couple in the center of the reactor permitted checking the catalyst temperature. Through suitable lines, measured amounts of ammonia, propylene and air in a molar ratio of 1.2 : 1 : 12 were fed to the catalyst obtaining a space velocity per hour of 50, calculated at atmospheric pressure and at room temperature.

The analysis of the reaction products was carried out by drawing a sample downstream of the reactor and by introducing it into a gas chromatograph provided with a flame ionization detector. At 480° C a conversion of 52.7% of propylene and a selectivity of acrylonitrile of 25% were obtained. At 500° C the conversion was 61.3% and the selectivity 23.2%.

In this example the low selectivity and activity of the catalyst constituted only of oxygenated compounds of iron and tungsten were pointed out.

EXAMPLE 2

By operating in a way similar to the procedure of Example 1, a catalyst was prepared based on oxycompounds of bismuth and tungsten supported on silica. To this end 31 g of $(NH_4)_2 0.12WO_3 \cdot 5H_2O$, 50 cc of $H_2O_2$ at 35% b.w., 48 g of $Bi(NO_3)_3 \cdot 5H_2O$ and 128 g of a solution of silica sol (Ludox) at 40% were used. Said catalyst produced the following results when it was tested under experimental conditions similar to those of the preceding example:

At 450° C the conversion of the propylene was 61% and the selectivity to acrylonitrile 33%; at 480° C the conversion was 76% and the selectivity 38%; at 500° C the conversion was 85% and the selectivity 30%.

Said example shows the oxycompounds of bismuth and tungsten supported on silica were not very active and scarcely selective catalysts.

EXAMPLE 3

87 g of 5 $(NH_4)_2 0.12WO_3 \cdot 5H_2O$ were weighed and dissolved in 200 cc of $H_2O_2$ at 35% b.w. Separately, 107 g of $Bi(NO_3)_3 \cdot 5H_2O$ and 22 g of $Fe(NO_3)_3 \cdot 9H_2O$ were dissolved in 20 cc of $HNO_3$ at 65% and 200 cc of $H_2O$. The solutions were put together at cold; 230 g of silica sol (Ludox) at 40% were added. The resulting solution was then heated to 100° C on an electrical heater, stirring from time to time until it was dried. The catalyst was activated at 550° C for 12 hours. 6 cc of catalyst having sizes of 45 – 140 ASTM mesh were introduced into the micro-reactor and the reaction was performed under the conditions described in Example 1. At 470° C there was a conversion of propylene of 90% with a selectivity to acrylonitrile of 58% and to acetonitrile of 65%. The presence of acrolein was not detected.

EXAMPLE 4

When heated, 56 g of tungsten trioxide were dissolved in 200 cc of an aqueous concentrated solution of ammonia; the solution was then diluted to 1000 cc with distilled water. Separately, 20 g of bismuth nitrate and 65 g of iron nitrate were dissolved in water and nitric acid. The second solution was added to the first one, then neutralized up to pH 7; the precipitate was permitted to form and then it was filtrated, washing repeatedly with water. The precipitate was dispersed in water so as to obtain a pulp at 10% of solid and it was dried through atomization by means of a spray-dryer. The powder recovered was compressed in tablets, activated at 550° C for 12 hours and milled.

A fraction of 6 cc was introduced into a micro-reactor; propylene, ammonia and air in the ratios of 1/1.2/10 were fed and it was operated as described in Example 1. At 480° C a 70% conversion of $C_3H_6$ and a 68% selectivity to acrylonitrile were obtained. At 490° C a 80% conversion of $C_3H_6$ and a 71.6% selectivity to acrylonitrile were obtained.

EXAMPLE 5

A catalyst was prepared according to the method of Example 3 but without the carrier. The catalyst, 6 cc, was tested at T = 445° C with a ratio propylene-ammonia-air-water equal to 1/1.3/11/10 at a space velocity of propylene of 50 cc per cc of catalyst per hour. For the propylene a conversion was determined of 97.1%, and a selectivity to acrylonitrile of 55.3%.

EXAMPLE 6

A catalyst, prepared according to Example 4, was tested by carrying out the reaction in a fluid bed. Into a stainless steel reactor having an internal diameter of 4.5 cm. heated from the outside by means of suitable electrical resistances, 500 cc of catalyst were put, having a granulometry comprised between 100 and 270 ASTM mesh. In the reactor a sinterized steel plate supported the catalyst and provided for the distribution of the reactants introduced to the bottom; a thermo-couple was placed in a suitable sheath along the vertical axis of the reactor for the control of the reaction temperature.

Propylene, ammonia and air were fed in the ratios 1/1.2/10 at such a flow to obtain a contact time of 5 sec. calculated at room temperature. At a temperature of 470° C a conversion of the propylene of 92.5%, a selectivity to acrylonitrile of 62.6%, a selectivity to acetonitrile of 4.6% and traces of acrolein were obtained.

EXAMPLE 7

28.4 g of Fe $(NO_3)_3$. $9H_2O$ together with 6.9 g of $H_6TeO_6$ were dissolved in $H_2O$. To this solution was added another one, which was obtained by dissolving 31.3g of $5(NH_4)_2O.12 WO_3. 5H_2O$ in $H_2O_2$ at 120 vol. At the end to the resulting solution 100 g of colloidal silica at 40% of $SiO_2$ were added. It was evaporated to dryness and after elimination of the nitrates, at a temperature between 200 and 250° C, the resulting solid was activated at 530° C for 4 hours in the presence of air. 6 cc of catalyst so obtained, reduced to a granulometry between 50 and 100 meshes, were put in a micro-reactor. A mixture was fed, constituted by:

$$C_3H_6/NH_3/air = 1/1.3/9.0$$

having a space velocity equal to 50 cc/cc h at the temperature of 465° C; a conversion of $C_3H_6$ was obtained equal to 85.0% with a selectivity to acrylonitrile of 67.0%.

What we claim is:

1. A process for the production of acrylonitrile comprising feeding propylene, ammonia and oxygen at ratios between 1/0.7/1 and 1/1.4/3 and at temperatures between 350° C, and 550° C, at pressures between 1 atm. and 5 atms. over a catalyst consisting essentially of, as the sole catalytic agent, one having the general formula:

$$W_a M_b Me_c^{viii} O_d$$

wherein W is tungsten; M is bismuth; $Me^{viii}$ is iron; and O is oxygen, wherein the tungsten is present in gram atomic amounts greater than the gram atomic amounts of each individual remaining metal component or the sum of the remaining metal components, wherein the metal components of the catalyst are in the form of oxygenated compounds, and wherein $a$ is 1; $b$ is 0.04 to 0.8; $c$ is 0.08 to 0.8; and $d$ is 2.5 to 9.5, said catalyst having been calcined at a temperature in the range of from 400° C. to 800° C. for from 1 to 60 hours.

2. A process as defined in claim 1 wherein said catalyst is supported on a support selected from the group consisting of silica and alumina.

3. A process as defined in claim 1 wherein the reaction temperature range is between 440° C. and 530° C.

4. A process as defined in claim 1 wherein the oxygen is fed as a component in oxygen-containing gas.

5. A process as defined in claim 1 wherein said catalyst has been calcined in the range of from 500° C. to 650° C.

* * * * *